US011058325B2

(12) United States Patent
Kostic et al.

(10) Patent No.: US 11,058,325 B2
(45) Date of Patent: Jul. 13, 2021

(54) PATIENT SUPPORT APPARATUSES WITH MULTI-SENSOR FUSION

(71) Applicant: Stryker Corporation, Kalamazoo, MI (US)

(72) Inventors: Marko N. Kostic, Johnson City, TN (US); Sujay Sukumaran, Portage, MI (US); Jonathan Mark Greenbank, Plainwell, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 16/367,872

(22) Filed: Mar. 28, 2019

(65) Prior Publication Data

US 2019/0298229 A1 Oct. 3, 2019

Related U.S. Application Data

(60) Provisional application No. 62/650,504, filed on Mar. 30, 2018.

(51) Int. Cl.
*A61B 5/11* (2006.01)
*A61B 5/00* (2006.01)
(Continued)

(52) U.S. Cl.
CPC .......... *A61B 5/1115* (2013.01); *A61B 5/6891* (2013.01); *A61C 5/85* (2017.02);
(Continued)

(58) Field of Classification Search
CPC ... A61B 5/1115; A61B 5/6891; G08B 21/043; G08B 21/0461; G08B 21/22; A61G 2203/46; A61G 7/05; A61G 2203/44; A61G 2203/36; A61G 7/0509; A61G 7/012; A61G 7/0524; A61G 2203/30; A61G 2203/32; A61G 2203/34; A61G 7/0506; A61G 7/08; A61G 7/0514; A61G 7/0515; A61G 7/015;
(Continued)

(56) References Cited

U.S. PATENT DOCUMENTS

| 5,276,432 A | 1/1994 | Travis |
| 9,754,476 B2 | 9/2017 | Lemire et al. |
| 9,940,810 B2 | 4/2018 | Derenne |
| 2003/0136908 A1* | 7/2003 | Pfister .................... G08B 29/24 250/338.1 |

(Continued)

*Primary Examiner* — Brian Wilson
(74) *Attorney, Agent, or Firm* — Warner Norcross + Judd LLP

(57) ABSTRACT

A patient support apparatus includes a plurality of primary sensors adapted to measure different parameters used in the control of the patient support apparatus. One or more suites of secondary sensors are added to the patient support apparatus to provide data about the primary sensors. The secondary sensors may be used to detect errors in the primary sensors, to modify outputs from the primary sensors, and/or to provide usage and/or diagnostic data about the use of the patient support apparatus. The suite(s) of secondary sensors may measure parameters that affect the outputs of one or more of the primary sensors. In some embodiments, the suite(s) of secondary sensors include one or more dormant sensors that are not used on the patient support apparatus until a code modification is received from one or more external sources instructing the control system of the patient support apparatus to begin using the dormant sensor(s).

17 Claims, 6 Drawing Sheets

(51) Int. Cl.
*G08B 21/04* (2006.01)
*A61C 5/85* (2017.01)
*A61C 9/00* (2006.01)
*A61C 13/15* (2006.01)
*A61C 19/05* (2006.01)
*A61G 7/05* (2006.01)
*G08B 21/22* (2006.01)

(52) U.S. Cl.
CPC .......... *A61C 9/0053* (2013.01); *A61C 19/004* (2013.01); *A61C 19/05* (2013.01); *G08B 21/043* (2013.01); *G08B 21/0461* (2013.01); *A61C 2201/002* (2013.01); *A61G 7/05* (2013.01); *A61G 2203/36* (2013.01); *A61G 2203/44* (2013.01); *A61G 2203/46* (2013.01); *G08B 21/22* (2013.01)

(58) Field of Classification Search
CPC ....... A61C 5/85; A61C 9/0053; A61C 19/004; A61C 19/05; A61C 2201/002
See application file for complete search history.

(56) References Cited

U.S. PATENT DOCUMENTS

| | | | |
|---|---|---|---|
| 2006/0028350 A1* | 2/2006 | Bhai | G01G 19/445 340/666 |
| 2006/0277683 A1* | 12/2006 | Lamire | A61G 7/015 5/600 |
| 2007/0157385 A1* | 7/2007 | Lemire | A61G 7/0509 5/600 |
| 2015/0323388 A1 | 11/2015 | Kostic et al. | |
| 2016/0022218 A1 | 1/2016 | Hayes et al. | |
| 2016/0106345 A1 | 4/2016 | Kostic et al. | |
| 2016/0128610 A1* | 5/2016 | Kostic | A61B 5/1115 5/613 |
| 2016/0193095 A1 | 7/2016 | Roussy et al. | |
| 2016/0374874 A1* | 12/2016 | Trepanier | A61G 1/04 5/611 |
| 2017/0003159 A1 | 1/2017 | Kostic et al. | |
| 2017/0098359 A1 | 4/2017 | Sidhu et al. | |
| 2017/0128296 A1 | 5/2017 | Kostic et al. | |
| 2017/0281440 A1 | 10/2017 | Puvogel et al. | |
| 2018/0153753 A1 | 6/2018 | Kostic et al. | |

* cited by examiner

PATIENT SUPPORT APPARATUSES WITH MULTI-SENSOR FUSION

CROSS-REFERENCE TO RELATED PATENT APPLICATIONS

This application claims priority to U.S. provisional patent application Ser. No. 62/650,504 filed Mar. 30, 2018, by inventors Marko Kostic et al. and entitled PATIENT SUPPORT APPARATUSES WITH MULTI-SENSOR FUSION, the complete disclosure of which is incorporated herein by reference.

BACKGROUND

The present disclosure relates to patient support apparatuses used to support patients in medical facilities, such as, but not limited to, beds, stretchers, cots, recliners, wheelchairs, operating tables, and the like.

Patient support apparatuses typically include a plurality of sensors used for carrying out the various functions of the patient support apparatus. These may include sensors for detecting the position, angle, speed, and/or acceleration of a movable component of the patient support apparatus, sensors for detecting a weight on the patient support apparatus, sensors for detecting a force exerted against the patient support apparatus, sensors for detecting a characteristic of a patient supported on the patient support apparatus, and/or other types of sensors. Such sensors, however, may produce erroneous results, due to wear and tear and/or other factors, and such sensors may only provide a limited and incomplete picture of the conditions being experienced by the patient support apparatus.

SUMMARY

According to several aspects of the present disclosure, a patient support apparatus is provided that includes one or more primary sensors that are used to carry out one or more functions of the patient support apparatus, and one or more secondary sensors that are used for detecting, compensating, and/or monitoring the outputs of the primary sensor(s). The secondary sensor(s) are not used, in some embodiments, other than to detect parameters that affect the primary sensor(s). Further, in some embodiments, multiple primary sensors are included and a suite of secondary sensors is associated with each of the multiple primary sensors. The secondary sensors may each be mounted to a common circuit board, or at some other location, adjacent to the associated primary sensor so that the parameters detected by the secondary sensors are local to that particular associated primary sensor. The outputs from one or more of the secondary sensors are fused together to provide a more complete picture of events, conditions, and/or the environment in which the patient support apparatus is operating. The patient support apparatuses may also include one or more dormant sensors that are not used until authorization is received from an external source, thereby activating the dormant sensor(s) and enabling the patient support apparatus to be field-upgraded to include new sensing abilities without the need to make any physical modifications to the patient support apparatus. These and other features of the present disclosure will be apparent in light of the following written description and accompanying drawings.

According to one aspect of the present disclosure, a patient support apparatus is provided that includes a frame, a support surface for supporting a patient thereon, a primary sensor, a primary controller, a suite of secondary sensors, and a secondary controller. The primary sensor is adapted to measure a primary parameter related to a component of the patient support apparatus and the primary controller is adapted to receive measurements of the primary parameter from the primary sensor. The suite of secondary sensors are adapted to measure a plurality of secondary parameters capable of affecting measurements made by the primary sensor. The secondary controller is adapted to process outputs from the suite of secondary sensors to detect if at least one of the secondary parameters has affected a measurement made by the primary sensor.

According to other aspects of the present disclosure, the secondary controller is further adapted to send a notification to the primary controller if the secondary controller detects that at least one of the secondary parameters has affected a measurement made by the primary sensor.

In some embodiments, the suite of secondary sensors includes one or more of the following: a humidity sensor, a pressure sensor, a gyroscope, a magnetometer, an accelerometer, a speed sensor, a temperature sensor, and an angle sensor.

The primary parameter may be one of a speed, a position, an acceleration, an orientation, and/or an angle of a movable component of the patient support apparatus, or of the entire patient support apparatus itself.

In some embodiments, the primary sensor includes a load cell adapted to detect a weight of a patient supported on the support surface and the suite of secondary sensors includes an accelerometer adapted to detect an acceleration of the load cell.

The primary controller and suite of secondary sensors are mounted to a common circuit board, in some embodiments.

The patient support apparatus further includes, in at least one embodiment, a second primary sensor adapted to measure a second primary parameter related to a second component of the patient support apparatus, and a second suite of secondary sensors. The second suite of secondary sensors is adapted to measure a second plurality of secondary parameters, wherein the second plurality of secondary parameters are the same as the plurality of secondary parameters.

According to another embodiment of the present disclosure, a patient support apparatus is provided that includes a frame, a support surface adapted to support a patient thereon, a scale system, a first sensor suite, a second sensor suite, and a controller. The scale system includes a plurality of load cells adapted to detect a weight of a patient supported on the support surface. The first sensor suite is associated with at least a first one of the load cells and is adapted to measure a plurality of non-weight parameters. The second sensor suite is associated with at least a second one of the load cells and is adapted to also measure the plurality of non-weight parameters. The controller is adapted to determine if at least one of the plurality of non-weight parameters has affected a weight measurement from the first one or second one of the load cells.

According to other aspects of the present disclosure, the first sensor suite is coupled to a first circuit board positioned adjacent the first one of the load cells, and the second sensor suite is coupled to a second circuit board positioned adjacent the second one of the load cells.

In some embodiments, the controller is further adapted to modify the weight measurement if the controller determines that at least one of the plurality of non-weight parameters has affected the weight measurement. Alternatively, or additionally, the controller may be adapted to issue an alert if the controller determines that at least one of the plurality of non-weight parameters has affected the weight measurement.

The plurality of non-weight parameters includes at least one of the following: humidity, air pressure, angular acceleration, linear acceleration, speed, temperature, geomagnetic orientation, position, and an angle.

In some embodiments, the first sensor suite is mounted to a first circuit board and the second sensor suite is mounted to a second circuit board. The first sensor suite is positioned adjacent to the first one of the load cells and the second circuit board is positioned adjacent to the second one of the load cells.

The first one of the load cells is coupled to a first beam, in some embodiments. In such embodiments, the first sensor suite includes a first and a second accelerometer adapted to detect bending of the first beam. Further, the second one of the load cells is coupled to a second beam and the second sensor suite includes a third and a fourth accelerometer adapted to detect bending of the second beam.

According to another aspect of the present disclosure, a patient support apparatus is provided that includes a frame, a support surfaced adapted to support a patient thereon, a first primary sensor, a first suite of secondary sensors, a second primary sensor, a second suite of secondary sensors, a primary controller, and a secondary controller. The first primary sensor is adapted to measure a first primary parameter related to a first component of the patient support apparatus. The first suite of secondary sensors is adapted to measure a first plurality of characteristics of the first primary sensor. The second primary sensor is adapted to measure a second primary parameter related to a second component of the patient support apparatus. The second suite of secondary sensors is adapted to measure a second plurality of characteristics of the second primary sensor. The primary controller is adapted to use the first and second primary parameters to control the patient support apparatus, and the secondary controller is adapted to process outputs from the first and second suites of secondary sensors to detect if an error exists in the first or second primary parameters.

According to other aspects of the present disclosure, the first plurality of characteristics of the first primary sensor include at least one of the following: an angle of the first primary sensor, a pressure experienced by the first primary sensor, an acceleration of the first primary sensor, a speed of the first primary sensor, a temperature of the first primary sensor, an ambient humidity of the first primary sensor, a geographical orientation of the first primary sensor, and a change in orientation of the first primary sensor.

In some embodiments, the first suite of secondary sensors is coupled to a first circuit board positioned adjacent the first primary sensor, and the second suite of secondary sensors is coupled to a second circuit board positioned adjacent the second primary sensor.

The secondary controller, in some embodiments, is coupled directly to the first and second suites of secondary sensors such that outputs from the secondary sensors of both the first and second suites of secondary sensors are routed to the secondary controller without relying on the primary controller.

The patient support apparatus, in some embodiments, also includes a plurality of wheels and a motor adapted to drive at least one of the plurality of wheels. In such embodiments, the first primary sensor is a force sensor adapted to detect a user-applied force and the primary controller is adapted to control the motor based on outputs from the force sensor.

In some embodiments, the second primary sensor is a force sensor adapted to detect a weight of a patient supported on the support surface.

A patient support apparatus according to another aspect of the present disclosure includes a frame, a support surface, a primary sensor, a dormant sensor, a controller, and a transceiver. The support surface is adapted to support a patient thereon. The primary sensor is adapted to measure a primary parameter related to a component of the patient support apparatus. The dormant sensor is adapted to measure a secondary parameter capable of affecting measurements of the primary parameter. The controller is adapted to control an aspect of the patient support apparatus using factory-installed code. The factory-installed code uses outputs from the primary sensor but not the dormant sensor. The transceiver is adapted to receive a code modification from an off-board device wherein the code modification modifies the factory-installed code such that the controller uses outputs from the dormant sensor.

According to other aspects of the present disclosure, the code modification causes the controller to send data from the dormant sensor to a remote server, causes the controller to use outputs from the dormant sensor to determine if an error exists in measurements of the primary parameter, and/or causes the controller to adjust outputs from the primary sensor based on outputs from the dormant sensor.

In some embodiments, the dormant sensor is adapted to detect a secondary parameter capable of affecting measurements of the primary parameter by the primary sensor. The secondary parameter may include one or more of the following: humidity, air pressure, angular acceleration, linear acceleration, speed, temperature, geomagnetic orientation, position, and an angle.

In those embodiments where the controller sends data from the dormant sensor to a remote server, the remote server may be adapted to process outputs from the dormant sensor to determine if an error condition exists with respect to the patient support apparatus.

In some embodiments, the primary sensor is a force sensor adapted to detect force exerted on the patient support apparatus, and the outputs from the force sensor are used to control a motor on the patient support apparatus or are used to determine a weight of a patient supported on the support surface.

In some embodiments, the code modification is an instruction to execute software that was previously loaded on the patient support apparatus but that remained unused until the instruction was received.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration is used in the description herein of various embodiments (e.g. first, second, third, etc.). Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
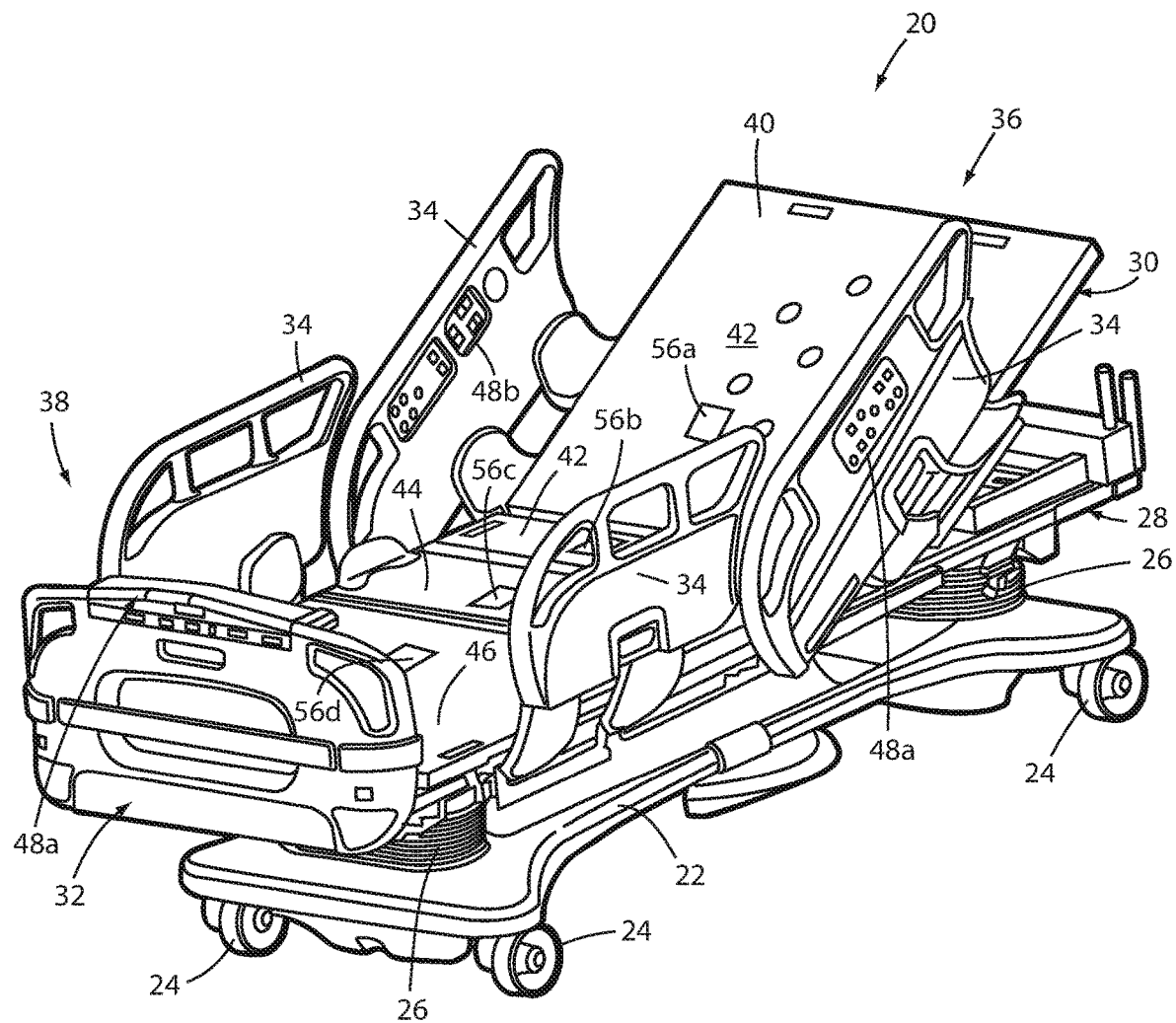
FIG. 1 is a perspective view of a patient support apparatus according to a first embodiment of the disclosure.

An illustrative patient support apparatus 20 according to a first embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, a wheelchair, or any other mobile structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a footboard 32 (which may be removable) and a plurality of siderails 34. Siderails 34 are all shown in a raised position in FIG. 1 but are each individually movable to a lower position in which ingress into, and egress out of, patient support apparatus 20 is not obstructed by the lowered siderails 34.

Lifts 26 are adapted to raise and lower litter frame 28 with respect to base 22. Lifts 26 may be hydraulic actuators, pneumatic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 36 and a foot end 38, each of whose height can be independently adjusted by the nearest lift 26. Patient support apparatus 20 is designed so that when a person lies thereon, his or her head will be positioned adjacent head end 36 and his or her feet will be positioned adjacent foot end 38.

Litter frame 28 provides a structure for supporting support deck 30, footboard 32, and siderails 34. Support deck 30 provides a support surface for a mattress (not shown), such as, but not limited to, an air, fluid, or gel mattress. Alternatively, another type of soft cushion may be supported on support deck 30 so that a person may comfortably lie and/or sit thereon. The top surface of the mattress or other cushion forms a support surface for the patient. Support deck 30 is made of a plurality of sections, some of which are pivotable about generally horizontal pivot axes. In the embodiment shown in FIG. 1, support deck 30 includes a head section 40, a seat section 42, a thigh section 44, and a foot section 46. Head section 40, which is also sometimes referred to as a Fowler section, is pivotable about a generally horizontal pivot axis between a generally horizontal orientation (not shown in FIG. 1) and a plurality of raised positions (one of which is shown in FIG. 1). Seat section 42, thigh section 44 and/or foot section 46 may also be pivotable about generally horizontal pivot axes. The pivot axes of those deck sections 40-46 that are pivotable in a particular embodiment of patient support apparatus 20 are oriented generally horizontally and perpendicular to the longitudinal extent (from head end 36 to foot end 38) of patient support apparatus 20.

Patient support apparatus 20 further includes a plurality of user interfaces 48 that enable a user of patient support apparatus 20, such as a patient and/or an associated caregiver, to control one or more aspects of patient support apparatus 20. In the embodiment shown in FIG. 1, patient support apparatus 20 includes a footboard user interface 48a, a pair of inner siderail user interfaces 48b (only one of which is visible), and a pair of outer siderail user interfaces 48c (only one of which is visible). Footboard user interface 48a and outer siderail user interfaces 48c are intended to be used by caregivers, or other authorized personnel, while inner siderail user interfaces 48b are intended to be used by the patient associated with patient support apparatus 20. Not all of the user interfaces 48 include the same controls and/or functionality. In the illustrated embodiment, footboard user interface 48a includes a substantially complete set of controls for controlling patient support apparatus 20 while user interfaces 48b and 48c include a selected subset of those controls.

The controls of user interfaces 48 allow a user to control one or more of the following: change a height of support deck 30, raise or lower head section 40, activate and deactivate a brake for wheels 24, arm and disarm an exit detection system, take a weight reading of the patient, activate and deactivate a propulsion system, and communicate with a healthcare facility computer network installed in the healthcare facility in which patient support apparatus 20 is positioned. Inner siderail user interfaces 48b may also include a nurse call control that enables a patient to call a nurse. A speaker and microphone are included in order to allow the patient to aurally communicate with the remotely positioned nurse.

Footboard user interface 48a is implemented in the embodiment shown in FIG. 1 as a control panel having a lid (flipped down in FIG. 1) underneath which is positioned a plurality of controls. The controls may be implemented as buttons, dials, switches, or other devices. Any of user interfaces 48a-c may also include a display for displaying information regarding patient support apparatus 20. The display may be a touchscreen in some embodiments.

As can be seen in FIG. 1, patient support apparatus 20 also includes a plurality of sensor suite circuit boards 56. More specifically, patient support apparatus 20 includes a head section sensor suite board 56a mounted to head section 40, a seat section sensor suite board 56b mounted to seat section 42, a thigh section sensor suite board 56c mounted to thigh section 44, and a foot section sensor suite board 56d mounted to foot section 46. These four sensors suite boards

56*a-d* are collectively part of a deck articulation system 78 (FIG. 6) that will be discussed in greater detail below. Each of these boards 56*a-d* is adapted to detect, among other things, deflection of the corresponding sections 40-46 of support deck 30 due to patient weight and/or other loads, as will be discussed in greater detail below. The position and/or number of these boards 56*a-d* may be changed from what is shown in FIG. 1.

Figure 2:
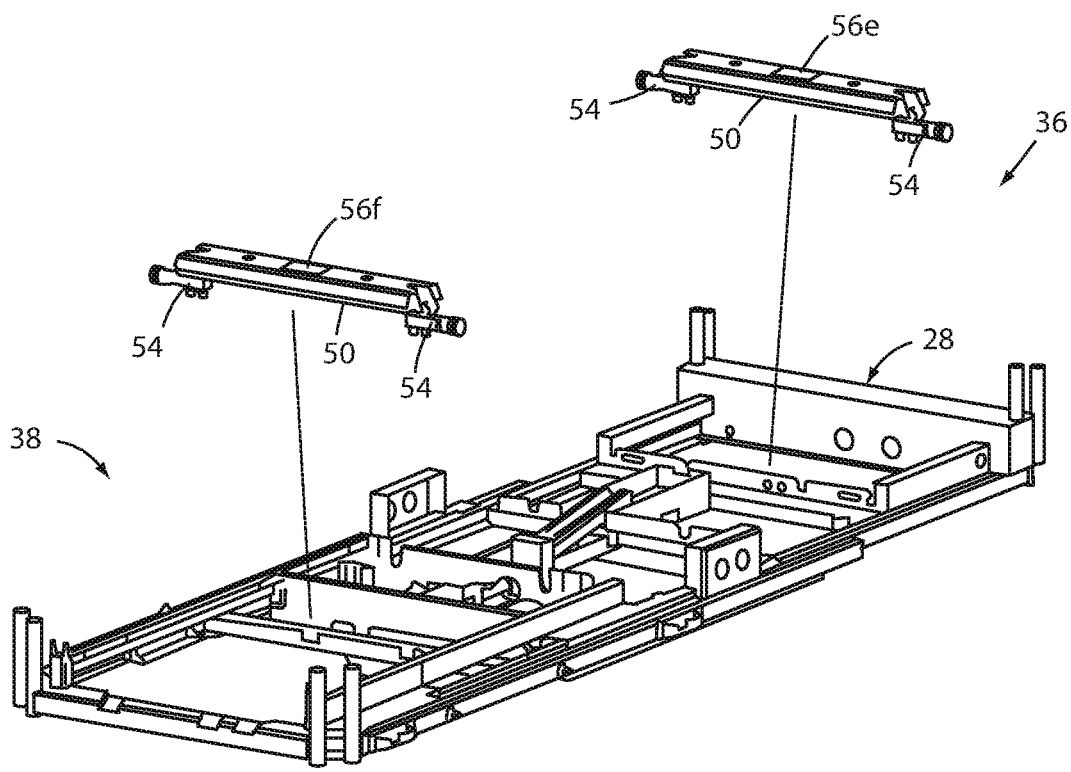
FIG. 2 is a perspective view of a litter frame of the patient support apparatus of FIG. 1 shown detached from the rest of the patient support apparatus.

FIG. 2 illustrates in greater detail litter frame 28 separated from lifts 26 and base 22. Litter frame 28 is also shown in FIG. 2 with support deck 30 removed. Litter frame 28 is supported by two lift header assemblies 50. A first one of the lift header assemblies 50 is coupled to a top 52 (FIG. 3) of a first one of the lifts 26, and a second one of the lift header assemblies 50 is coupled to the top 52 of the second one of the lifts 26. Each lift header assembly 50 includes a pair of load cells 54. Load cells 54 may be replaced by other force sensors, including, but not limited to, linear variable displacement transducers and/or any one or more capacitive, inductive, and/or resistive transducers that are configured to produce a changing output in response to changes in the force exerted against them.

Although the illustrated embodiment of patient support apparatus 20 includes a total of four load cells 54 (FIG. 3), it will be understood by those skilled in the art that different numbers of load cells 54 may be used in accordance with the principles of the present disclosure. Load cells 54 are configured to support litter frame 28. More specifically, load cells 54 are configured such that they provide complete and exclusive mechanical support for litter frame 28 and all of the components that are supported on litter frame 28 (e.g. support deck 30, footboard 32, the headboard, siderails 34, etc.). Because of this construction, load cells 54 are adapted to detect the weight of not only those components of patient support apparatus 20 that are supported by litter frame 28 (including litter frame 28 itself), but also any objects or persons who are wholly or partially being supported by support deck 30.

Load cells 54 are part of a scale/exit detection system 76 (FIG. 6) that is integrated into patient support apparatus 20. Scale/exit detection system 76 functions to provide an alert when a patient exits, or is about to exit, from patient support apparatus and/or measures the weight of the patient and/or objects positioned on litter frame 28. In some embodiments of patient support apparatus 20, only the scale function of scale/exit detection system 76 is utilized and patient support apparatus 20 is able to measure a patient's weight, but not issue an alert when a patient exits, or is about to exit, from patient support apparatus 20. In other embodiments of patient support apparatus 20, only the exit detection function of scale/exit detection system 76 is utilized and patient support apparatus 20 is only able to issue an alert when a patient exits, or is about to exit from, patient support apparatus 20, but is not able to measure the weight of the patient. In still other embodiments, both the scale and exit detection functions of scale/exit detection system 76 are utilized and the patient support apparatus is both able to issue exit alerts and weigh the patient. Still further, in some embodiments, scale/exit detection system 76 may be adapted to monitor the movement of the patient and/or objects positioned on support deck 30, and use such movement monitoring for purposes other than issuing an exit alert.

Load cells 54 are adapted to detect downward forces exerted by an occupant of support deck 30. Thus, when an occupant is positioned on support deck 30 and substantially still (i.e. not moving in a manner in which patient acceleration forces are exerted against support deck 30), load cells 54 detect the weight of the occupant (as well as the weight of any components of patient support apparatus 20 that are supported—directly or indirectly—by load cells 54). This enables the system 76 to determine a weight of the patient.

In some embodiments, load cells 54 are also or alternatively used to determine a center of gravity of the occupant for purposes of monitoring patient movement. This enables system 76 to monitor patient movement and determine when a patient has exited from, and/or is about to exit from, litter frame 28. Alternatively, the exit detection function may be implemented by analyzing the outputs from load cells 54, not to determine a center of gravity, but instead to determine a weight distribution and/or a change in weight distribution, such as by determining one or more ratios of the relative weights sensed by the load cells 54. Other types of sensors may also or alternatively be used for determining the occupant's weight and/or movement instead of load cells.

When load cells 54 are used to monitor patient movement and, in some cases, issue an exit detection alert, load cells 54 operate in accordance with the principles disclosed in the following commonly assigned U.S. patent references: U.S. Pat. No. 5,276,432 issued to Travis and entitled PATIENT EXIT DETECTION MECHANISM FOR HOSPITAL BED; and U.S. patent application Ser. No. 62/253,167 filed Nov. 10, 2015, by inventors Marko Kostic et al. and entitled PERSON SUPPORT APPARATUSES WITH ACCELERATION DETECTION, the complete disclosures of both of which are incorporated herein by reference. Other algorithms for using the load cells 54 may also be used for detecting a patient's presence, absence, exit, and/or other movement.

As can be seen in FIG. 2, patient support apparatus 20 also includes a head lift sensor suite circuit board 56*e* and a foot lift sensor suite circuit board 56*f*. Each of these boards 56*e*, 56*f* is part of scale/exit detection system 76 and each of these boards 56*e*, 56*f* is coupled to a corresponding beam of one of the lift header assemblies 50. Board 56*e* is adapted to process the outputs from the two load cells 54 positioned adjacent head end 36 of patient support apparatus and board 56*f* is adapted to process the outputs from the two load cells 54 positioned adjacent foot end 38 of patient support apparatus 20. As will be discussed in greater detail below, each board 56*e*, 56*f* may also be adapted to detect, among other parameters, bending of the lift header assemblies 50 (specifically, the beam or other structure of the lift header assembly to which the circuit boards 56*e*, 56*f* are mounted). In alternative embodiments, boards 56*e* and 56*f* may be positioned in different locations from what is shown in FIG. 2.

The rest of the mechanical construction of patient support apparatus 20 not described herein may be the same as the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that patient support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of patient support apparatus 20 may also take on forms different from what is disclosed in the aforementioned references.

Figure 4:
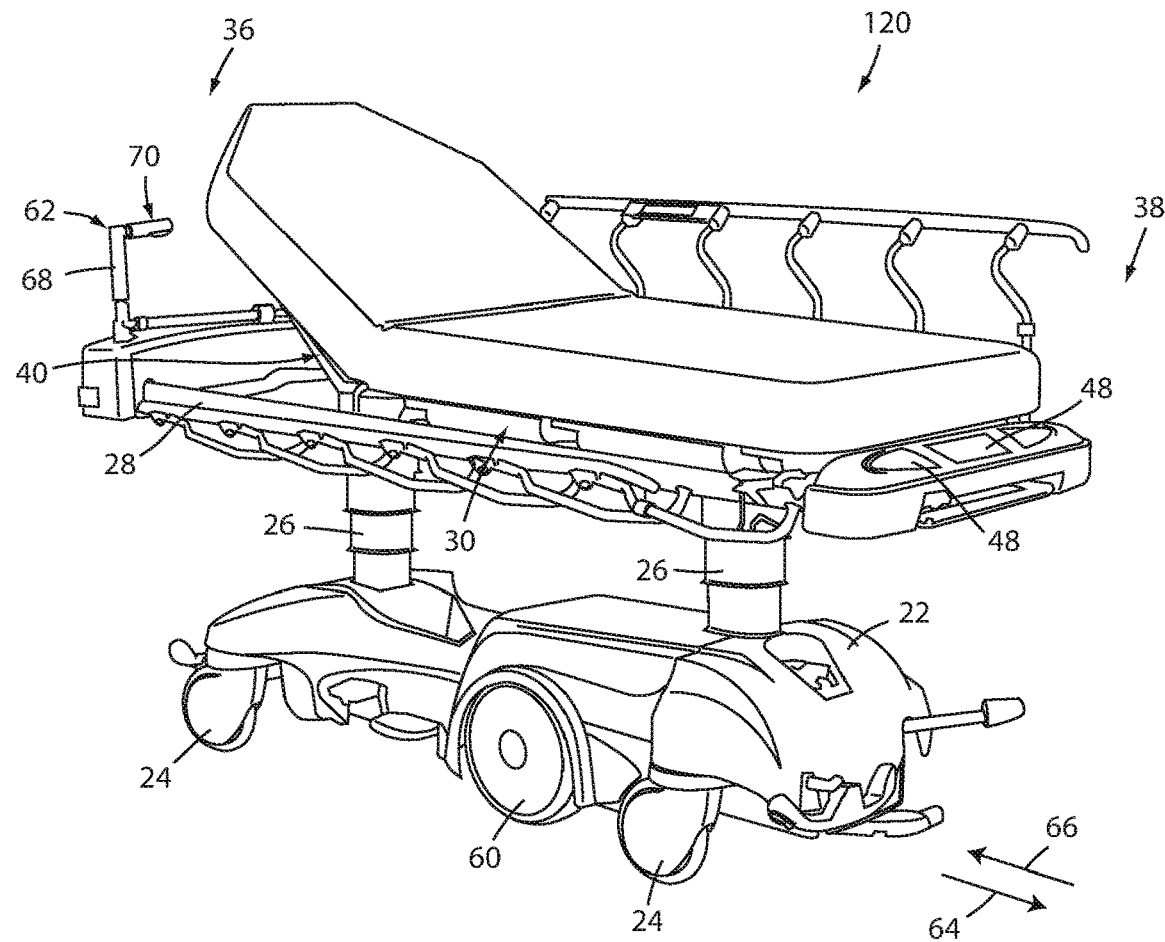
FIG. 4 is a perspective view of a patient support apparatus according to a second embodiment of the disclosure.

Turning to FIG. 4, a patient support apparatus 120 according to another embodiment of the present disclosure is shown. Those components of patient support apparatus 120 that are common to patient support apparatus 20 are provided with the same reference number and, unless other stated herein, operate in the same manner and/or provide the same functionality. Those components of patient support apparatus 120 that are not found in patient support apparatus 20 are provided with a new reference number.

Patient support apparatus 120 differs from patient support apparatus 20 in that patient support apparatus 120 is a stretcher, rather than a bed. Patient support apparatus 120 also differs from patient support apparatus 20 in that it includes a motorized propulsion system 58. The motorized propulsion system 58 includes at least one driven wheel 60 and a pair of propulsion control handles 62 (only one of which is visible in FIG. 4). Propulsion system 58 drives driven wheel 60 in either a forward direction 64 or a rearward direction 66 depending upon whether a user pushes or pulls on propulsion control handles 62. This enables patient support apparatus 120 to be moved to different locations without requiring a caregiver to supply all of the forces necessary to move patient support apparatus 120.

In some embodiments, patient support apparatus 120 may utilize a propulsion system of the type disclosed in more detail in commonly assigned U.S. patent application Ser. No. 15/471,361 filed Mar. 28, 2017, by inventors Thomas Puvogel et al. and entitled PATIENT SUPPORT APPARATUSES WITH DRIVE SYSTEMS, the complete disclosure of which is incorporated herein by reference. In other embodiments, propulsion system 58 may be constructed in any of the manners and/or include any one or more of the features or functions of the systems disclosed in any one or more of the following commonly assigned U.S. patents and/or patent application Ser. No. 15/189,149 filed Jun. 22, 2016, by inventors Jerald Trepanier et al. and entitled PERSON SUPPORT APPARATUSES WITH DRIVE CONTROLS; Ser. No. 15/185,067 filed Jun. 17, 2016, by inventors Michael Joseph Hayes et al. and entitled PATIENT SUPPORT APPARATUSES WITH NAVIGATION AND GUIDANCE SYSTEMS; U.S. Pat. No. 9,259,369 issued to Derenne et al. and entitled POWERED PATIENT SUPPORT APPARATUS; U.S. Pat. No. 6,772,850 issued to Waters et al. and entitled POWER ASSISTED WHEELED CARRIAGE; and U.S. Pat. No. 8,442,738 issued to Patmore and entitled SPEED CONTROL FOR PATIENT HANDLING DEVICE, the complete disclosure of all of which are incorporated herein by reference.

Figure 5:
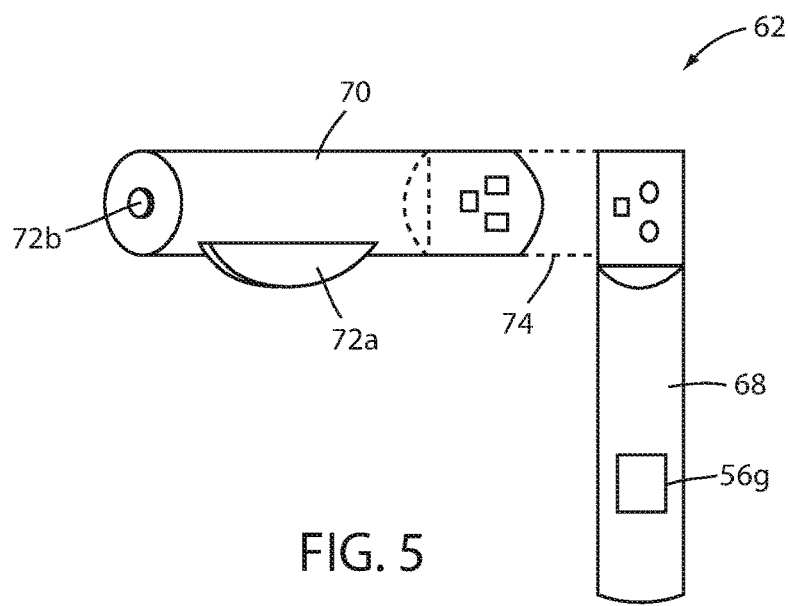
FIG. 5 is an elevation view of a propulsion control handle of the patient support apparatus of FIG. 4.

FIG. 5 illustrates in greater detail one of the propulsion control handles 62 of propulsion system 58. Handle 62 includes a post 68, a handlebar 70, one or more enable switches 72a, b, and a load cell 74. In some embodiments, only a single enable switch 72 is utilized, while in other embodiments, no enable switches 72 are used. When included, enable switches may operate in the manner disclosed in commonly assigned U.S. patent application Ser. No. 15/189,149 filed Jun. 22, 2016, by inventors Jerald Trepanier et al. and entitled PERSON SUPPORT APPARATUSES WITH DRIVE CONTROLS, the complete disclosure of which is incorporated herein by reference. In brief overview, when a user has activated one or both of the enable switches 72a and or 72b, the users pushing or pulling on handlebar 70 is detected by load cell 74 and used to control the movement of patient support apparatus 120. More specifically, the force detected by the load cell is used to send generate commands that are sent to a motor for driving driven wheel 60. Patient support apparatus 120 can therefore be driven by a user who controls the movement of patient support apparatus 120 via handles 62.

In the embodiment shown in FIG. 5, handle 62 also includes a propulsion sensor suite circuit board 56g. Propulsion sensor suite circuit board 56g is shown mounted inside of post 68, but it will be understood that it may be positioned in other locations, such as, but not limited to, handlebar 70. The operation and function of circuit board 56g will be discussed in more detail below with respect to FIG. 6 and the circuit boards 56 illustrated therein.

Figure 6:
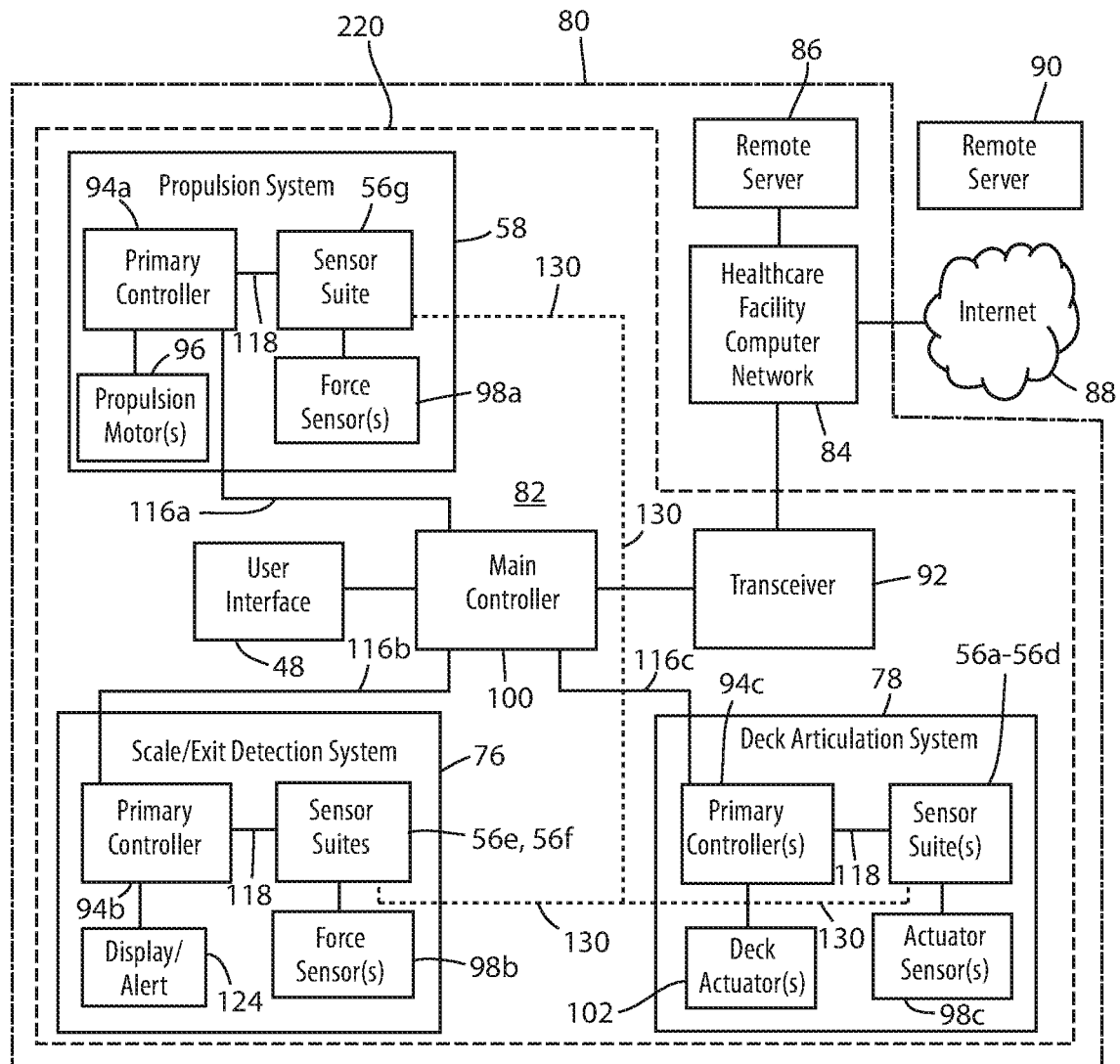
FIG. 6 is a block diagram of a patient support apparatus according to a third embodiment of the present disclosure shown in communication with one or more remote servers.

FIG. 6 illustrates a patient support apparatus 220 positioned within a healthcare facility 80. Patient support apparatus 220 includes a number of components that are common to either or both of patient support apparatuses 20 and 120. Such components are provided with the same reference numbers as found in these previously described patient support apparatuses and, unless otherwise explicitly indicated, operate in the same manner. Patient support apparatus 220 also includes one or more components that are present in one or both of patient support apparatuses 20 and/or 120 but which have not yet been described and/or assigned a reference number. Such components have been given a new reference number.

Patient support apparatus 220 is a patient support apparatus that combines together several features of patient support apparatus 20 and patient support apparatus 120. Specifically, patient support apparatus 220 includes the scale/exit detection system 76 and the deck articulation system 78 of patient support apparatus 20, as well as the propulsion system 58 of patient support apparatus 120. It will be understood by those skilled in the art that the combination of systems 58, 76, and 78 into a single patient support apparatus 220 has been done herein merely to consolidate the description of these systems and to illustrate that these systems are optionally combinable in a particular patient support apparatus. To that end, it will be understood that patient support apparatuses 20, 120, and 220 provide only three examples of the types of patient support apparatuses that may be implemented in accordance with the principles disclosed herein. Other types of patient support apparatuses that may implement the principles herein include those having a different combination of two of the systems of FIG. 6 (e.g. a scale/exit detection system 76 combined with a propulsion system 58, but no deck articulation system 78), those having only a single one of the systems 58, 76, and/or 78 of FIG. 6, and/or those having one or more other systems not shown in FIG. 6 that operate in accordance with the principles disclosed herein and that are incorporated into the patient support apparatus either alone or in combination with any one or more of the systems 58, 76, and/or 78 of FIG. 6.

Patient support apparatus 220 includes a control system 82 that is adapted to, among other things, communicate with a healthcare facility computer network 84 that includes at least one server 86. In the illustrated embodiment, healthcare facility computer network 84 is also coupled to the Internet 88, thereby allowing patient support apparatus 220 to communicate with at least one remote server 90 positioned outside of the healthcare facility 80. Control system 82 communicates with healthcare facility computer network 84 and one or both of servers 86, 90 via one or more network transceivers 92. Network transceivers 92 may be implemented for wired or wireless communication. When implementing wireless communication, network transceivers 92 are adapted to communicate with one or more wireless access points (not shown) of healthcare facility network 84. In some such embodiments, network transceivers 92 are WiFi transceivers (IEEE 802.11) adapted to communicate with the access points using any of the various WiFi protocols (IEEE 802.11b, 801.11g, 802.11n, 802.11ac . . . , etc.). In other embodiments, network transceivers 92 are adapted to wirelessly communicate using any of the frequencies, protocols, and/or standards disclosed in commonly assigned U.S. patent application Ser. No. 62/430,500 filed Dec. 6, 2016, by inventor Michael Hayes and entitled NETWORK COMMUNICATION FOR PATIENT SUPPORT APPARATUSES, the complete disclosure of which is incorporated herein by reference. In still other embodiments, network transceivers 92 communicate via wired communication, such as, but not limited to, an Ethernet cable.

Control system 82 also includes a main controller 100 that is in communication with systems 58, 76, and 78 via communication lines 116a, 116b, and 116c, respectively. Communication lines 116a-c may take on a variety of different forms, such as, but not limited to, a Controller Area Network connection, an Ethernet connection, an I-Squared-C connection, an RS-485 connection, etc. Control system 82 also includes one or more user interfaces 48 that enable a user to control and operate patient support apparatus 220.

Propulsion system 58 includes a primary controller 94a, one or more propulsion motors 96, one or more sensor suite boards 56g, and one or more primary sensors 98a. In this particular implementation of propulsion system 58, primary sensors 98a include one or more force sensors, such as the previously-discussed force sensors 74 of FIG. 4. Motor 96 is adapted to drive one or more driven wheels 60 and primary sensors 98a are adapted to detect a user pushing or pulling against handlebars 70. Primary sensors 98a may be implemented as load cells or other types of force sensors, as noted above with respect to force sensors 74.

Propulsion system 58 (FIG. 6) is adapted to drive one or more driven wheels 60 in response to forces applied by a user to patient support apparatus 220. Propulsion system 58 accomplishes this by feeding the outputs of primary force sensors 98a to sensor suite board 56h, which monitors and analyzes these outputs to determine the magnitude and direction of forces applied to patient support apparatus 220. These forces are fed to primary controller 94a which, in turn, uses them to send the appropriate commands to motor(s) 96 in order to move patient support apparatus 220 in a manner corresponding to the user-applied forces. In some embodiments, propulsion system 58 includes one or more enable switches 72 that must be activated first before primary controller 94a sends any movement commands to motor(s) 96, as discussed previously.

Scale/exit detection system 76 (FIG. 6) includes a primary controller 94b, one or more displays 124 and/or other types of alerting devices 124, a pair of sensor suite boards 56e, 56f, and a plurality of primary sensors 98b. Primary sensors 98b include force sensors 54 discussed above with respect to patient support apparatus 20, and such sensors may be load cells and/or other types of force sensors. Display/alert 124 may be a graphical display, such as, but not limited to, a Liquid Crystal Display (LCD), and/or may include one or more audio, visual, and/or audiovisual devices for issuing audio and/or visual alerts when a patient is detected as exiting, or being about to exit, from patient support apparatus 220. Such audio devices may include a buzzer, beeper, speaker, or the like, and such visual devices may include one or more lights that are selectively illuminated in a particular manner to indicate the presence of an exit detection alert.

Scale/exit detection system 76 measures a patient's weight and/or detects a patient's exit by feeding the outputs from primary sensors 98b to sensor suite boards 56e, 56f. In this particular embodiment, two of the primary sensors 98b (e.g. load cells 54 of FIG. 2) located at the head end 36 of the patient support apparatus feed their outputs to first sensor suite board 56e and another two of the primary sensors 96b (e.g. load cells 54 of FIG. 2) located at the foot end 38 of the patient support apparatus feed their outputs to a second sensor suite board 56f. It will be understood that this arrangement may be varied. In some modified embodiments, all of primary sensors 98b (e.g. four load cells 54) feed into a single sensor suite board 56, while in other modified embodiments, each primary sensor 98b includes its own individual sensor suite board 56. Still other modifications are possible.

Each sensor suite board 56e, 56f of scale/exit detection system 76 processes the outputs from the respective primary sensors 98 and feeds the processed outputs to primary controller 94b. Primary controller 94b determines the weight of the patient and/or whether the patient is about to exit from patient support apparatus 20 based on the data received from sensor suite boards 56e, 56f. When it determines a weight, primary controller 94b forwards the weight reading to display 124. When it determines that a patient has exited, or is likely to exit, primary controller 94b forwards an activation signal to alert 124 commanding it to start an audio, visual, and/or audiovisual alert. In some embodiments, primary controller 94b may forward the weight and/or exit detection alert to main controller 100 which, in turn, may forward the received information to one or both of the remote servers 86 and 90.

Deck articulation system 78 (FIG. 6) includes a primary controller 94c, one or more deck, actuators 102, a plurality of sensor suite boards 56a-56d, and a plurality of primary sensors 98c. Each deck actuator 102 is adapted to pivot a section of patient support deck 30, such as head section 40, seat section 42, thigh section 44, and/or foot section 46. Deck actuators 102 may take on a variety of different forms. In some embodiments, actuators 102 are linear actuators of the type disclosed in commonly assigned U.S. patent application Ser. No. 15/449,277 filed Mar. 3, 2017, by inventors Anish Paul et al. and entitled PATIENT SUPPORT APPARATUS WITH ACTUATOR FEEDBACK, the complete disclosure of which is incorporated herein by reference. In other embodiments, other types of actuators may be used.

Primary sensors 98c of deck articulation system 78 include any one or more sensors adapted to detect a position and/or angle of each of deck sections 40-46 of patient support deck 30. In some embodiments, primary sensors 98c include one or more motor encoders that monitor movement of a motor contained within each actuator 102. In other embodiments, primary sensors 98c may include one or more limit switches of the types disclosed in the aforementioned commonly assigned Ser. No. 15/449,277 patent application. Still other types of sensors may be used for monitoring the position and/or angle of those sections of support deck 30 that are pivotable.

Deck articulation system 78 controls the pivoting of such deck sections based upon commands received from a user. Those commands are input into control system 82 via one or more of the user interfaces 48. The commands are received by main controller 100, which forwards the commands to primary controller 94*c* of deck articulation system 78. Alternatively, the commands from one or more of the user interfaces 48 may be sent directly to primary controller 94*c*, thereby bypassing main controller 100. Primary controller 94*c* is programmed to send commands to the corresponding actuator(s) 102 to move the deck section(s) 40-46 in the desired direction. When moving a deck section 40-46, primary controller 94*c* is configured to utilize the outputs of primary sensors 98*c* as feedback. Such feedback may be used for speed control, acceleration control, and/or for determining when to stop movement of one or more of the deck sections 40-46.

Each of the sensor suites boards 56 includes a plurality of secondary sensors 104 that are adapted to detect additional information that may affect the readings generated from primary sensors 98 and/or that may detect additional useful information for other purposes. An illustrative example of one sensor suite board 56 is shown in more detail in FIG. 7. As can be seen therein, sensor suite board 56 includes a plurality of secondary sensors 104*a*-104*g*. In many embodiments, each of these secondary sensors 104 is physically mounted to the printed circuit board that makes up sensor suite board 56. In such embodiments, the secondary sensors 104 are physically positioned on the printed circuit board and therefore measure parameters local to the environment of that particular printed circuit board. As will be discussed more below, because secondary sensors 104 are often adapted to detect parameters that are capable of affecting the outputs from the corresponding primary sensor 98, each sensor suite board 56 may be desirably positioned adjacent to the primary sensor 98 so that the secondary sensors 104 detect parameters of the local environment in which the primary sensor 98 is positioned.

Figure 7:
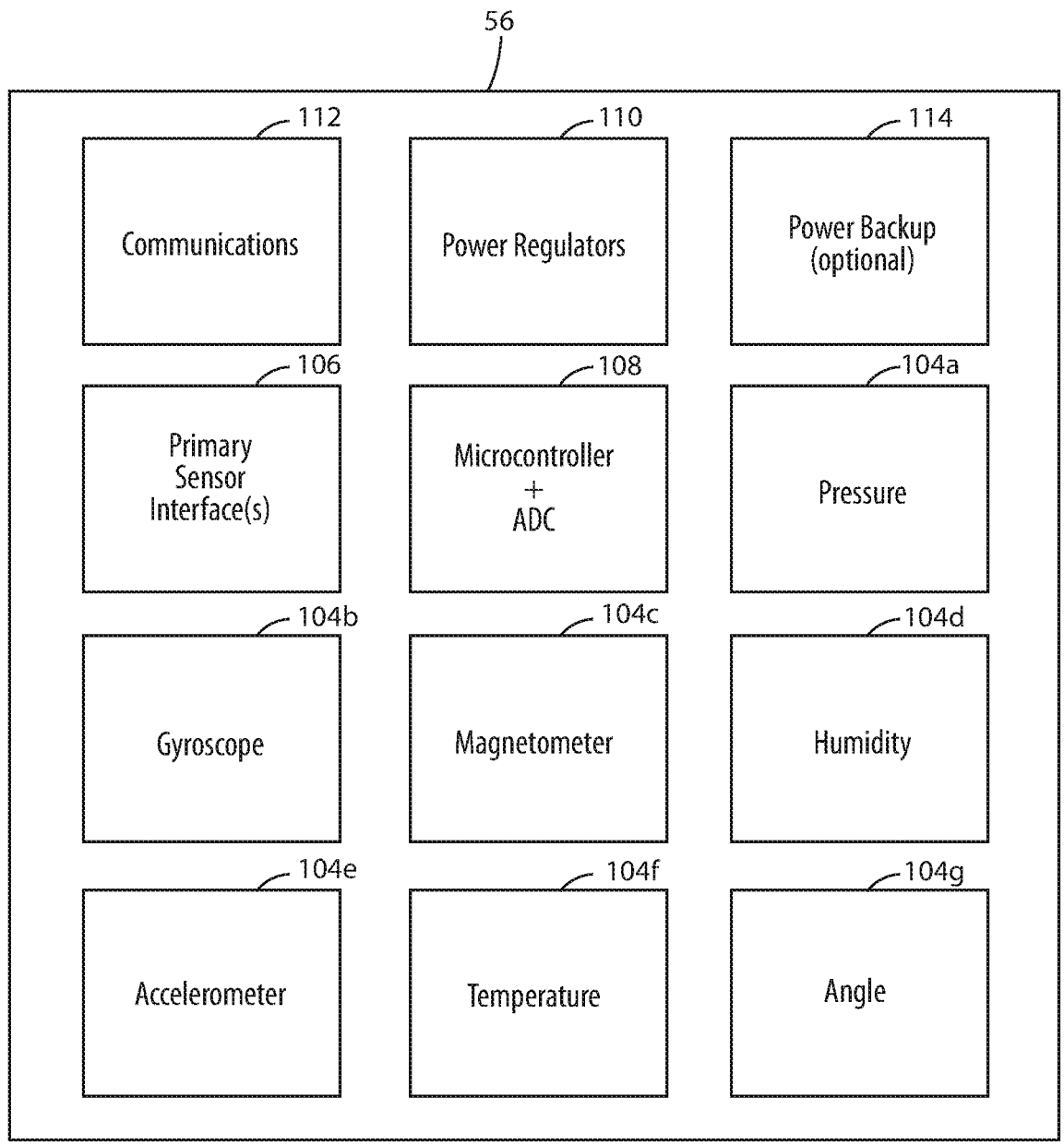
FIG. 7 is a block diagram of a representative sensor suite board used in the patient support apparatuses disclosed herein.

In the example sensor suite board 56 of FIG. 7, sensor 104*a* is a pressure sensor adapted to detect ambient air pressure; sensor 104*b* is a gyroscope adapted to detect changes in orientation (relative to one, two, or three orthogonal axes); sensor 104*c* is a magnetometer adapted to detect magnetic fields, including the geomagnetic field and its relative orientation thereto; sensor 104*d* is a humidity sensor adapted to detect humidity in the ambient air and/or moisture on a surface; sensor 104*e* is an accelerometer adapted to detect changes in acceleration (along one, two, or three orthogonal axes); sensor 104*f* is a temperature sensor adapted to detect the temperature of ambient air and/or the temperature of a device or surface; and sensor 104*g* is an angle sensor adapted to detect the angle of sensor suite board 56 relative to a known reference, such as, but not limited to, a vertical gravity vector or another component of the patient support apparatus.

It will be understood by those skilled in the art that the particular selection of secondary sensors 104 shown in the example of FIG. 7 is but one example of among many different variations. Sensor suite board 56 may be modified to include more than one of any of the secondary sensors 104 shown in FIG. 7; may be modified to omit one or more of the particular secondary sensors 104 shown in FIG. 7; and/or may be modified to add other secondary sensors 104 that are not shown in FIG. 7. Further, it will be understood that not all of the sensor suite boards 56 (if multiple ones are included on a particular patient support apparatus) need be identical. Thus, for example, sensor suite board 56*e* and 56*f* of scale/exit detection system 76 may have a different assortment of secondary sensors 104 than sensor suite board 56*g* of propulsion system 58, while sensor suite boards 56*a*-56*d* of deck articulation system 78 may have the same selection of secondary sensors 104 that are found on sensor suite boards 56*e* and 56*f*. Other combinations are possible. Still further, in some embodiments, the sensor suite boards 56 within a given system (e.g. 58, 76, and/or 78) may have different selections of secondary sensors 104, although in most embodiments the secondary sensors 104 used within a given system are the same.

In addition to the secondary sensors 104, each sensor suite board 56 also includes a primary sensor interface 106, a secondary controller 108, a power regulator 110, and a communications interface and/or transceiver 112 (FIG. 7). In some embodiments, a backup power supply 114 may also be included in order to provide backup power if power from power regulator 110 fails. Primary sensor interface 106 is adapted to interface with one or more of the primary sensors 98 used in the corresponding system of which sensor suite board 56 is a part. For example, in propulsion system 58, primary sensor interface 106 couples to primary sensor 98*a* (e.g. load cells 74). In scale/exit detection system 76, primary sensor interface 106 couples to force sensors 98*b* (e.g. load cells 54). In deck articulation system 78, primary sensor interface 106 couples to actuator sensors 98*c*. In some embodiments, where it is suitable, the primary sensor 98 is mounted directly to sensor suite board 56, or sensor suite board 56 is mounted directly to the primary sensor 98. By doing so, the primary sensor 98 is positioned more closely to the secondary sensors 104, and the readings of the secondary sensors 104 may provide a more accurate picture of the conditions experienced by the primary sensor 98 due to the smaller physical distance between them.

Power regulator 110 (FIG. 7) regulates the electrical power necessary to operate each of the secondary sensors 104, secondary controller 108, interface 106, and communications transceiver 112. Power regulator 110 is a conventional circuit, in at least some embodiments. Communications transceiver 112 enables communications between secondary controller 108 and its corresponding primary controller 94. To that end, communication transceiver 112 couples to communication lines 118 between each sensor suite board 56 and its associated primary controller 94 (FIG. 6). Communication lines 118 may be any suitable serial or parallel communication form, including, but not limited to, a Controller Area Network connection, an Ethernet connection, an I-Squared-C connection, an RS-485 connection, etc.

Communications transceiver 112 also allows direct communication between a secondary controller 108 of a first sensor suite board 56 and one or more other secondary controllers 108 of other sensor suite boards 56. Such communication between secondary controllers 108 is able to take place independently of the communication between secondary controller 108 and primary controllers 94 (as well as independently of main controller 100). That is, secondary controllers 108 are able to communicate with each other over an independent onboard communication network 130 that does not rely on any primary controller 94 or main controller 100. In this manner, not only is a secondary controller 108 able to fuse together the data from the multiple secondary sensors 104 mounted to its sensor suite board 56, it is also able to fuse together the sensor data from secondary sensors 104 that are mounted to other sensor suite boards 56. This fusion of data from multiple sensor suite boards 56 enables the system of secondary sensors to develop a more complete and/or accurate assessment of the conditions and/or environment in which the patient support apparatus is operating.

Independent onboard communication network 130 may take on a variety of suitable forms, such as, but not limited to, a Controller Area Network (CAN), an Ethernet, an RS-485 network, and I-Squared-C network, or still another type of communication structure. In an alternative embodiment, secondary controllers 108 communicate with each other through their associated primary controller 94 and communication lines 116, 118.

Each controller (main controller 100, primary controllers 94a-c, and secondary controller 108) in patient support apparatus 220 is, in at least one embodiment, a conventional microcontroller. The particular brand and/or model of microcontrollers used for each controller may vary within the same embodiments. For example, in one embodiment, main controller 100 is from the i.MX family of system-on-chip (SoC) processors and one or more of the other controllers (primary and secondary controllers 94 and 108) are from the Kinetis K60 family of microcontroller units (MCUs), both of which are marketed by Freescale Semiconductor of Austin, Tex. Other microcontroller units, of course, may be used. In general, the controllers 94, 100, and 108 include any and all electrical circuitry and components necessary to carry out the functions and algorithms described herein, as would be known to one of ordinary skill in the art. Such circuitry may include one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. The instructions followed by the controllers 94, 100, and 108 in carrying out the functions described herein, as well as the data necessary for carrying out these functions, are stored in one or more accessible memories.

For each sensor suite board 56, the primary sensor 98 sends its outputs to sensor interface 106, which puts the received outputs into a form acceptable for processing by the secondary controller 108 (FIG. 7). Each secondary controller 108 also receives outputs from each of the secondary sensors 104 that are present on that particular sensor suite board 56. Secondary controller 108 uses the outputs from secondary sensors 104 in one or more of the following manners, depending upon the particular embodiment of patient support apparatus 220:

(1) it processes the outputs to determine if one or more errors are likely present in the outputs from the primary sensor 98 and, if so, corrects the outputs from the primary sensor 98 before sending them to the associated primary controller 94;

(2) it processes the outputs from the secondary sensors 104 to determine if any errors are likely present in the outputs from the primary sensor 98 and, if so, sends an error message to the associated primary controller 94 along with the uncorrected outputs from the primary sensor 98;

(3) it processes and monitors the outputs from the secondary sensors 104 looking for anomalies or readings that exceed one or more predefined thresholds or criteria and, if detected, shares such anomalies with one or more other secondary controllers 108 and/or its associated primary controller 94;

(4) it conditionally sends the outputs from one or more secondary sensors 104 to its associated primary controller 94 in order to enable primary controller 94 to use the outputs to better carry out its primary function;

(5) it sends the outputs from one or more selected secondary sensors 104 to one or more other systems (e.g. 58, 76, 78), via communication line 118 and/or secondary network 130;

(6) it sends the outputs from all, or a programmed selection, of the secondary sensors 104 to one or both of the remote servers 86, 90;

(7) it logs the outputs from the secondary sensors 104 in a non-volatile memory and time stamps the readings;

(8) it does nothing with one or more of the secondary sensor outputs until modified software is installed on patient support apparatus that updates the factory-installed software, wherein the modified software includes instructions for using the outputs from one or more of the secondary sensors 104; and (9) it does any combination of options (1)-(8) with any one or more of the outputs from one or more of the secondary sensors 104.

These nine different options for secondary controller 108 to process the outputs from one or more of the secondary sensors 104 can be better understood with respect to a number of examples that follow. In any of the first seven options, the secondary controller 108 may fuse together the data from multiple ones of the secondary sensors 104 as part of its processing of data. Such fusing may take on a variety of forms including, but not limited to, looking for correlations from the sensor data, looking for one or more pre-defined patterns in the sensor data, and/or using the sensor data from multiple sensors to confirm or refute the occurrence of an event (e.g. a collision) and/or the presence/absence of a particular condition (e.g. high or low air pressure).

The first option for processing the secondary sensor data may be better understood with respect to scale/exit detection system 76. When scale/exit detection system 76 is implemented with load cells 54 as the primary force sensors 98b in the manner shown in FIGS. 2 and 3, the outputs from the load cells 54 will include errors if the load cells 54 are oriented such that the applied forces are not aligned with the sensing directions of the load cells. That is, most load cells are configured to sense a load applied in a particular direction. If the load is applied to the load cell in a direction that is not aligned with that sensing direction, only the vector component of the applied load (if any) that is aligned with the sensing direction is detected.

Figure 3:
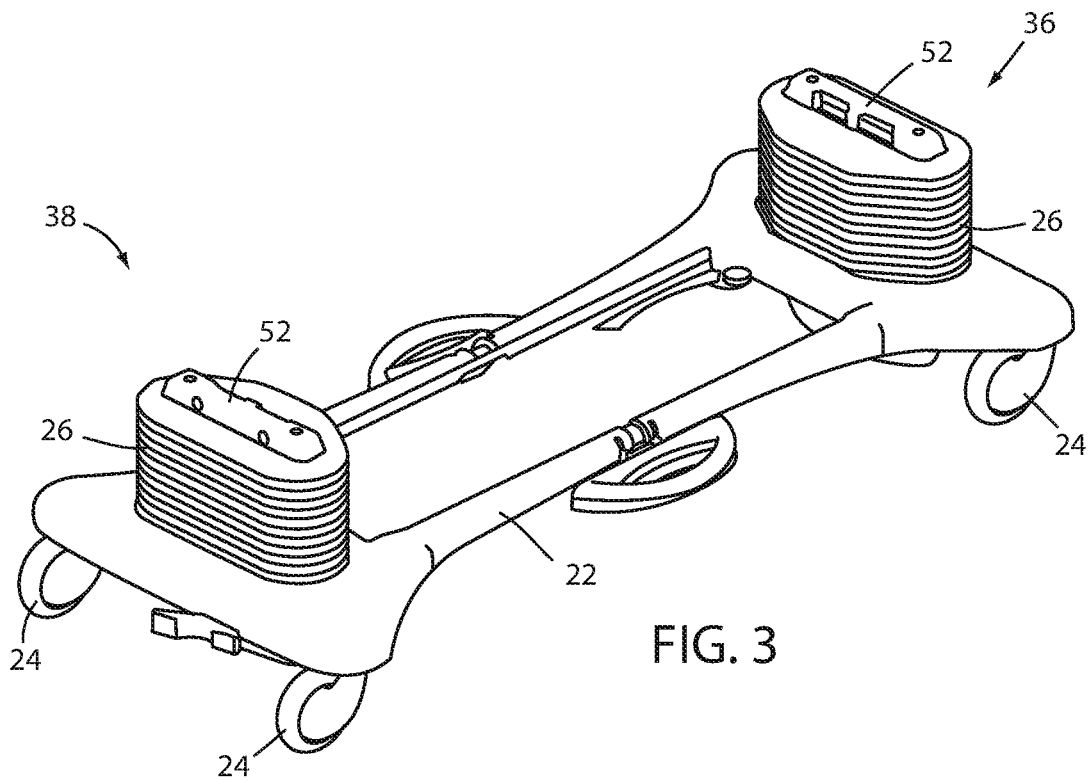
FIG. 3 is a perspective view of a base and pair of lifts of the patient support apparatus of FIG. 1 shown detached from the rest of the patient support apparatus.

Thus, with respect to the example of FIGS. 2-3, if the lift header assemblies 50 of patient support apparatus 20 are subjected to a load that bends or twists them such that the load cell sensing direction is no longer completely vertical (which is the orientation used to sense the gravitational weight of the patient and/or other items on the patient support apparatus), the load cells will not sense the total force applied to them, but will instead only sense the vector component of the applied weight that is vertical. In this situation, secondary sensor suite boards 56e and 56f may each be used to detect any deformations in their corresponding lift header assemblies 50 that lead to load cells 54 being shifted out of proper alignment with respect to the applied load. Specifically, one or more accelerometers 104e and/or angle sensors 104g may be used for this purpose. In such a situation, secondary controller 108 uses the appropriate trigonometric ratio(s) (determined from the known geometry of the sensors 104 relative to the load cells 54 and the sensing direction of the load cells 54) to correct the outputs from the corresponding load cells 54 before sending them to the primary controller 94. In this manner, secondary sensors 104 and secondary controller 108 are able to correct the outputs of the load cells 54 prior to their being processed by the primary controller 94 which, as noted above, may use them to compute a weight and/or to determine if a patient has exited, is about to exit, and/or to monitor movement of the patient or other objects on the support deck 30.

Secondary sensor suite boards 56e and 56f may also be used to correct the outputs from load cells 54 if the load cells are sensitive to other measurable parameters. For example, if load cells 54 are used that have outputs that are temperature dependent, secondary controller 108 may use the outputs from temperature sensor 104f (FIG. 7) to correct the load cell outputs before sending them to primary controller 94. Similarly, if the load cells 54 are sensitive to humidity, air pressure, magnetic fields, or other parameters, one or more of the outputs from the humidity sensor 104d, air pressure sensor 104a, magnetometer 104c or other types of secondary sensors 104 may be used by secondary controller 108 to correct the load cell outputs before sending them to primary controller 94.

An example of the second option identified above in which secondary controller 108 processes the outputs from one or more secondary sensors 104 is better understood with respect to one or more primary sensors 98 whose outputs vary with respect to one or more parameters in a way that is not easily correctable. For example, load cells 54 and/or 74 are typically only able to detect with accuracy a set of forces that fall within a specified range. If forces are applied that are outside of this range, then the outputs from the load cells 54 and/or 74 may not be accurate, but the errors in the outputs might not be easily correctable. In such situations, secondary controller 108 processes the outputs from the secondary sensors 104 (e.g. load cells) to determine if the measured parameter has exceeded a specified range, which is indicative of a likely error in the reading, and secondary controller 108 forwards the outputs from the primary sensor 98 to primary controller 94 without making any corrections or other adjustments to the outputs. Instead of correcting the outputs, secondary controller 108 forwards an error message or error warning to primary controller 94 indicating that the outputs may be incorrect.

The detection of a weight applied to a load cell 54 and/or 74 that is outside its acceptable operating range may be detected by one or more secondary sensors 104 in different manners. In many situations, an out-of-range weight is detected through the use of one or more accelerometers 104 and/or angle sensors 104 that detect deflection of the component of the patient support apparatus to which they are mounted. For example, in the case of scale/exit detection system 76, if excessive weight is applied to load cells 74, this results in a certain degree of downward deflection of the outer ends of lift header assemblies 50, which can be detected by one or more accelerometers 104e and/or one or more angle sensors 104g (and/or other types of secondary sensors). In the case of propulsion system 58, excessive pulling or pushing on handlebars 70 can be detected by measuring the deflection of posts 68, which can be sensed by one or more accelerometers 104e and/or angle sensors 104g (or other types of secondary sensors).

In some embodiments, secondary sensors 104 are used to detect when a primary sensor 98 is operating outside of an acceptable operating range with respect to a parameter other than the parameter that is sensed by primary sensor 98. That is, in addition to an acceptable range of applied forces, a force sensor 98 may also have an acceptable range of other parameters, such as an acceptable range of humidity, temperature, and/or other parameters in which it is intended by its manufacturer to operate within. When any of these ranges are exceeded, the force sensor 98 may not be guaranteed to operate accurately. Any of patient support apparatuses 20, 120, and/or 220 can utilize one or more secondary sensors 104 to sense whether such acceptable ranges are maintained or violated, and if violated, secondary controller is configured to issue an alert to primary controller 94.

The third option identified above for the processing of the outputs of one or more secondary sensors 104 by secondary controller 108 is to look for anomalies or readings that exceed one or more predefined thresholds or criteria and, if detected, share such anomalies with one or more other secondary controllers 108 and/or an associated primary controller 94. An example of this option can be better understood with respect systems 58, 76, and 78 of patient support apparatus 220. In any of these systems, the occurrence of anomalies in the secondary sensors outputs, or the presence of sensor values in the secondary sensor outputs that meet one or more other predefined conditions, is used to detect the occurrence of specific events. For example, if the accelerometers 104e of any of sensor suite boards 56 detects a sudden acceleration that exceeds a predefined magnitude, this is likely indicative of the corresponding patient support apparatus (20, 120, or 220) colliding with an object (a wall, another patient support apparatus, a medical device, furniture, etc.). In such situations, secondary controller 108 analyzes the outputs from the secondary sensors 104 to determine if the conditions have been satisfied for concluding that such a collision has actually occurred. If the conditions have been satisfied, secondary controller 108 sends a message to its associated primary controller 94, one or more other secondary controllers 108, and/or main controller 100. Still further, in some embodiments, as will be discussed more below, secondary controller 108 may share such information with other secondary controller 108 before deciding whether a collision has, in fact, occurred. Such sharing includes analyzing the outputs from the corresponding secondary sensors 104 from other sensor suite boards 56. That is, if a collision occurs with the patient support apparatus, all of the accelerometers 104e of the sensor suite boards 56 should detect the collision, and such sharing of their data can be used to more accurately verify whether a collision has occurred or not. Other events besides collisions may also, or alternatively, be detected using secondary sensors 104.

As noted above, the fourth option for secondary controller 108 to process the outputs from one or more of the secondary sensors 104 is to send the outputs to primary controller 94 in order to enable primary controller 94 to use the outputs to better carry out its primary function. An example of this type of processing can be better understood with respect to deck articulation system 78. In at least one embodiment of deck articulation system 78, secondary sensors 104 are used to detect deflection of each of the deck sections 40-46. These deflections correlate to the size of the load that is being supported on each of the deck sections 40-46, and secondary controller 108 processes their outputs in order to tell primary controller 94c how much load to expect when it raises or lowers one of the corresponding deck sections via its corresponding deck actuator 102. In other words, primary controller 94c of deck articulation system 78 uses the outputs from one or more secondary sensors 104 of sensor suite boards 56a-56d to adjust the manner in which it sends actuation commands to deck actuators 102. If a heavy load is being applied to head section 40, for example, primary controller 94 is adapted, in at least one embodiment, to more smoothly accelerate the movement of head section 40 via head section actuator 102, thereby subjecting the patient to less jerky movement. The reduction of the jerkiness in the motion of any of the deck sections 40-46 can be especially helpful in cases where the patient supported on support deck 30 is recovering from surgery and/or is suffering from another malady in which sudden movements are detrimental. By monitoring how much weight is applied to each individual section 40-46 of deck 30, primary controller 94*c* is able to adjust the movement of these deck sections in a way that subjects the patient supported thereon (if present) to smaller accelerations.

The fifth option for secondary controller 108 to process the outputs from one or more of the secondary sensors 104 is to send the outputs from the selected secondary sensors 104 to one or more other systems (e.g. 58, 76, 78), via communication line 118 and/or secondary network 130. One example of this type of processing was discussed above where at least some of the secondary sensors 104 are used to detect a collision, but the secondary sensors 104 used for such detection share their data prior to a secondary controller 108 determining that such a collision has actually occurred. In such situations, the secondary controller 108 forwards the outputs of its collision detection sensors 104 to another secondary controller 108 having collision detectors 104 on its associated sensor suite board 56. In some embodiments, the collision sensors 104 from more than two sensor suite boards 56 are compared and analyzed before detection of a collision is confirmed.

As another example of the fifth option for processing the outputs of one or more secondary sensors 104, deck articulation system 78 is configured, in at least one embodiment, to forward the outputs from its deflection sensors 104 to propulsion system 58. Such deflection sensors (which may be accelerometers and/or angle sensors) provide an indication of the distribution of the weight across the various deck sections 40-46. Primary controller 94*a* is configured to use this information when determining how much power to apply to propulsion motors 96 and/or how fast to accelerate propulsion motors 96. Certain weight distributions of the patient and/or equipment on support deck 30 represent situations where reduced acceleration of the patient support apparatus 20 may be desirable in order to reduce discomfort to the patient, to reduce the likelihood of an object rolling or tipping, or for other purposes.

In at least one embodiment, the outputs from one or more secondary sensors 104 of sensor suite boards 56*e*, 56*f* are used to detect when patient support apparatus 20, 120, and/or 220 is currently positioned on an inclined surface (e.g. floor). This condition may be detected by accelerometers 104*e*, or by other secondary sensors. When a non-level condition is detected, secondary controller 108 of scale/exit detection system 76 forwards this information to deck articulation system 78 (e.g. primary controller 94*c*). Primary controller 94*c* of deck articulation system 78 is configured, in some embodiments, to utilize this information to automatically adjust one or more of the deck sections 40-46 in such a way so as to maintain the patient's orientation and position that existed before the patient support apparatus was moved to the incline. Alternatively, rather than maintaining the patient's orientation and position, primary controller 94*c* automatically moves the deck sections 40-46 in a manner that reduces the accelerations experienced by the patient when the patient support apparatus is moved from a horizontal surface to an inclined surface, or vice versa. In this manner, the patient experiences less jostling when being transported to different locations within a hospital where such transport traverses uneven floors and/or sloped floors. Such a reduction in jostling is beneficial for patients recovering from surgery and/or suffering other medical maladies.

According to another alternative, one of patient support apparatuses 20, 120, and/or 220 is configured to forward outputs from one or more secondary sensors 104 that detect an uneven floor to a lift system controller (not shown). Such a lift system controller controls the actuation and height of lifts 26. In such embodiments, the lift controller is adapted to raise or lower one or both of the lifts 26 in order to adjust the slope of litter frame 28 in a manner that overcomes the slope of the sensed incline. That is, the lift controller adjusts the slope of litter frame 28 such that it remains level, despite the patient support apparatus being on a floor having an incline or a decline. Alternatively, or additionally, the lift system may be configured to maintain the patient in the same, or similar, non-level orientation when the patient support apparatus moves onto or off of an incline, such as a Trendelenburg orientation or a reverse-Trendelenburg orientation.

As another alternative, one or more of the outputs from air pressure sensors 104*a* are processed by one or more secondary sensors 104 and their processed outputs are sent to a location determining system (not shown) on board the patient support apparatus (20, 120, or 220). The air pressure sensors 104*a* are used to detect changes in the height of the patient support apparatus by sensing changes in barometric pressure as the patient support apparatus 20 is moved to different levels (floors) of a healthcare facility. Although changes in barometric pressure naturally occur in response to changing meteorological conditions, the movement of patient support apparatus 20 between floors causes relatively sudden changes in barometric pressure. By dividing the total amount of such relatively quick barometric pressure variations by a typical barometric pressure change for movement between a single floor, the on-board location system can detect how many floors the patient support apparatus is being moved up or down (such as on an elevator) within a healthcare facility. Further, by being initially told what floor it is on and thereafter keeping track of all such changes in its floor location, the location system can automatically determine what floor of a building it is on at all times by keeping track of all subsequent pressure changes.

The location information gathered from air pressure sensors 104*a* may be used with other location information gathered by the on board location system in order for the patient support apparatus to determine its location. Alternatively, the location information derived from air pressure sensors 104*a* may be forwarded off of the patient support apparatus via transceiver 92 to a remote server (e.g. 86, 92) that uses it to determine and keep track of the location of the patient support apparatus. In some embodiments, the floor information derived from air pressure sensors 104*a* is combined with the location information gathered from other on-board sensors of the type disclosed in commonly assigned U.S. Pat. No. 9,838,836 issued Dec. 5, 2017, to inventors Michael Hayes et al. and/or with other on-board sensors of the type disclosed in commonly assigned U.S. Pat. No. 9,937,090 issued Apr. 10, 2018, to inventors Michael Joseph Hayes et al.

The sixth option for secondary controller 108 to process the outputs from one or more of the secondary sensors 104 is to send the outputs from the selected secondary sensors 104 to one or more servers, such as remote server 86 and/or remote server 90. In some embodiments, the remote server uses the information from the secondary sensors 104 to monitor and gather data about the real world usage of the patient support apparatus. In other embodiments, the remote server stores the data for retrieval, such as when the patient support apparatus experiences an error or failure, or is otherwise undergoing service. In still other embodiments, the remote server processes the data for diagnostic purposes and/or for service determination purposes. In the latter case, the server may monitor how the patient support apparatus is being used and the conditions of its use in order to determine when the patient support apparatus should next be serviced. In such embodiments, the remote server may communicate with, or perform any of the functions, of the servers disclosed in commonly assigned U.S. patent application Ser. No. 15/786,699 filed Oct. 18, 2017, by inventors Krishna Bhimavarapu et al. and entitled SERVICE SCHEDULING AND NOTIFICATION SYSTEMS FOR PATIENT SUPPORT APPARATUSES, the complete disclosure of which is incorporated herein by reference. The remote server 86 and/or 90 may also process the data received from one or more of the secondary sensors in still other manners.

In some embodiments, the remote server (86, 90) that receives the outputs from one or more of the secondary sensors 104 is configured to provide alerts to appropriate personnel within the healthcare facility. In such cases, the remote server (86, 90) may be configured to send an alert whenever any condition detectable by one or more of the secondary sensors is actually detected. For example, in some healthcare facilities it is desirable to pressurize one or more rooms at a level greater than ambient pressure so that germs, viruses, bacteria, etc. that are present outside of the room are less likely to migrate into the room. Conversely, some healthcare facilities may have one or more rooms which are pressurized at a level below atmospheric pressure so that any germs, viruses, bacteria, etc. that are present inside that particular room are less likely to migrate outside of the room and into other areas of the hospital, or into the atmosphere. In either situation, air pressure sensors 104a are able to detect the air pressure and send data to the remote server when they detect an air pressure change of a magnitude and/or duration that is outside an acceptable limit. In response, the remote server sends an alert to one or more personnel of the healthcare facility notifying them of the pressure change. In such embodiments, the patient support apparatus may include a control on one or more of the user interfaces 48 allowing a user to activate this pressure-change alerting feature, while in other embodiments, the patient support apparatus may automatically activate this feature upon detecting ambient pressure conditions that deviate from atmospheric pressure by more than a threshold.

The seventh option for secondary controller 108 to process the outputs from one or more of the secondary sensors 104 is to simply time-stamp and store the outputs in a memory on board the patient support apparatus. In this option, the outputs are stored for potential subsequent retrieval, but are not used during the operation of the patient support apparatus. The retrieval of the recordings from the on-board memory may be desirably carried out when a service technician is attempting to fix a problem with the patient support apparatus and/or performing other service on the patient support apparatus. The data may also be retrieved for still other purposes and/or at other times.

The eighth option for secondary controller 108 to process the outputs from one or more of the secondary sensors 104 is to simply do nothing until software is loaded onto the patient support apparatus that tells secondary controller to process one or more of the outputs. In such a situation, the one or more secondary sensors 104 whose outputs are not processed by secondary controller 108 are referred to as dormant sensors. Such dormant sensors are provided on the patient support apparatus but are not used until a software modification is received. That is, the patient support apparatus is sold with factory-installed software that enables the patient support apparatus to function, but does not utilize the outputs from the dormant sensors for any purpose. In some embodiments, the patient support apparatus (20, 120, and/or 220) is configured such that the dormant sensors are only switched to a non-dormant state when a customer of the patient support apparatus pays additional money in order to activate a feature of the patient support apparatus that utilizes the dormant sensor 104. In other configurations, the dormant sensors are activated under other circumstances that need not involve the payment of additional money, such as adding one or more features, performing diagnostic checks, and/or in other situations. The software modification that activates the dormant sensor(s) is sent, in some embodiments, from a remote server, such as server 86 and/or 90. In other embodiments, the software modification may be installed onto the patient support apparatus locally—such as through a wired USB connection, a wireless Bluetooth connection, a WiFi connection, etc. —between the patient support apparatus and a computing device in which the software modification is stored. In still other configurations, a combination of these activation techniques is used for different dormant sensors 104.

The activation of the dormant sensors 104 into an active (non-dormant) state involves receiving software that is executed by secondary controller 108 and that instructs secondary controller 108 what to do with the previously dormant sensor. In some embodiments, the updated software to be executed by secondary controller 108 is received by a primary controller 94 and/or main controller 100 and stored in a memory location where it will be executed by secondary controller 108. Alternatively, in some embodiments, patient support apparatus 20, 120, and/or 220 includes dormant software already stored on board the patient support apparatus instructing secondary controller 108 how to process the outputs of the secondary sensors 104, but such dormant software is not loaded and/or executed by secondary controller 108 until a software instruction is received from remote server 86 or 90 telling secondary controller 108 to load and execute the dormant software. Such an instruction may be received by main controller 100 and/or primary controller 94, and either or both of those controllers then takes appropriate steps to cause secondary controller 108 start executing the dormant software.

In still other embodiments, no instruction to change a dormant sensor or dormant software into a non-dormant state is received from an off-board device, but instead such a change is carried out as a function of the software executed by main controller 100 and/or by a primary controller 94. In such embodiments, main controller 100 and/or a primary controller 94, in addition to their other functions, are programmed to change the dormancy state of a secondary sensor 104 or the software for a secondary controller 108 when certain criteria are met. Such criteria may vary. In some embodiments, if an error is detected, controller 100 and/or 94 activates the dormant sensor(s) and/or dormant software in order to see if additional information can be gathered regarding the error. The software of controller 100 and/or 94 may also, or alternatively, use one or more primary sensor readings that meet one or more thresholds to trigger a change from a dormant to a non-dormant state. Still further, the passage of a predetermined amount of time may trigger such a change. The software executed by controllers 100 and/or 94 may also include instructions for changing a non-dormant sensor or non-dormant software back into a dormant state based on any suitable criteria, including, but not limited to, the passage of a predetermined amount of time, the completion of a specified number of readings, and/or the completion of a diagnostic check.

Regardless of how a dormant sensor 104 is activated into a non-dormant state, the dormant sensor 104 is thereafter utilized by secondary controller 108 in any of the manners discussed herein. That is, the non-dormant sensor 104 has its outputs processed by its secondary controller according to any one or more of the other eight options mentioned above.

The ninth option for secondary controller 108 to process the outputs from one or more of the secondary sensors 104 is to process the outputs in accordance with a combination of any two or more of the previous eight options. That is, secondary controller 108 may process the outputs from one or more secondary sensors 104 in multiple ways.

Figure 8:
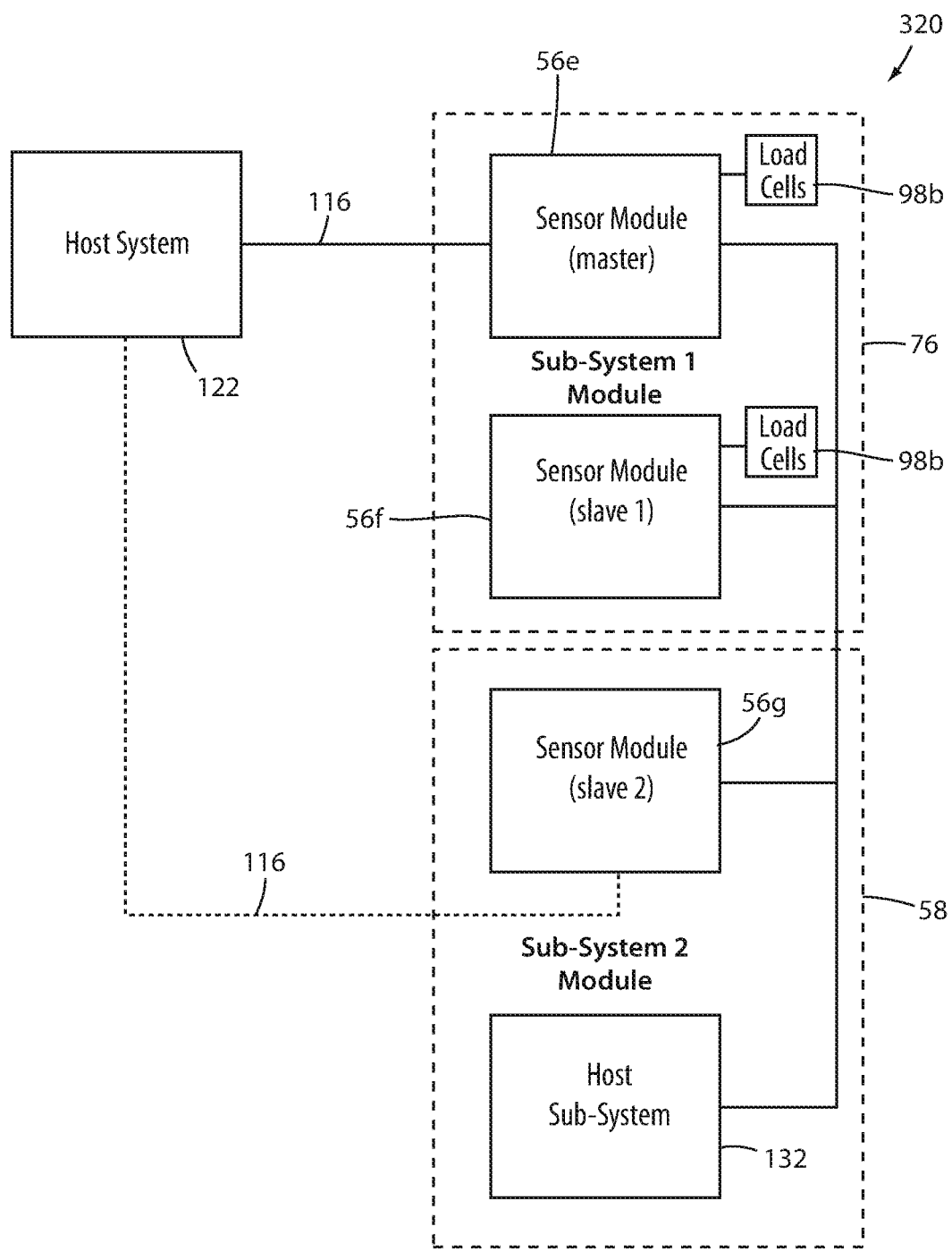
FIG. 8 is a block diagram of an alternative architecture of sensor suite boards and other components that may be used in any of the patient support apparatuses disclosed herein.

FIG. 8 illustrates an alternative architecture for incorporating several sensor suite boards 56 into a patient support apparatus 320. Although patient support apparatus 320 of FIG. 8 has been given a new reference number different from patient support apparatuses 20, 120, and 220, it will be understood that patient support apparatus 320 may be constructed to include any of the features, structures, and/or functions of patient support apparatus 20, 120, and/or 220, in any desirable combination. As depicted in FIG. 8, patient support apparatus 320 includes a scale/exit detection system 76, a propulsion system 58, and a host system 122. Host system 122 includes a main controller 100 (not shown), as well as a number of other components common to patient support apparatuses 20, 120, and/or 220. Host system 122 is coupled to scale/exit detection system 76 and propulsion system 58 by way of communication lines 116.

Scale/exit detection system 76 of patient support apparatus 320 differs from the previously described scale/exit detection system 76 in that it does not include a primary controller, nor does it include its own display/alert 124. Instead, sensor suite board 56e acts as a master controller for both sensor suite board 56e and sensor suite board 56f. Sensor suite board 56e processes the outputs from two of the primary force sensors 98 (e.g. load cells) and sensor suite board 56f processes the outputs from the other two primary force sensors 98 (e.g. load cells). Alternatively, sensor suite board 56f may be constructed to omit its secondary controller 108 and leave the processing of its secondary sensors and load cells 98b to the secondary controller 108 of sensor suite board 56e.

The secondary controller 108 of master sensor suite board 56e is configured, in at least one embodiment, to process the load cell signals from its two coupled load cells (and, in some embodiments, from all four load cells of system 76) to determine a weight of a patient, movement of the patient, and/or whether the patient is about to exit from patient support apparatus 320, or already has exited. This differs from the previously described scale/exit detection system 76 in that the determination of a patient exit, weight, and/or movement was performed by primary controller 94b. Scale/exit detection system 76 of FIG. 8 therefore combines the processing functions of primary controller 94b and at least one of the secondary controllers 108 into a single controller integrated into sensor suite board 56e.

Scale/exit detection system 76 of FIG. 8 also differs from the scale/exit detection system of FIG. 6 in that it does not include its own dedicated display/alert 124. Instead, any display and/or alerts that are used to display the measured weight, movement, and/or exit detection event, is incorporated into host system 122. Such a display/alert 124 may therefore be used by other components and/or systems of patient support apparatus 320.

Scale/exit detection system 76 of FIG. 8 may also be modified such that main controller 100 is programmed to process the outputs of load cells 98b, rather than the secondary controller of master sensor suite board 56e. It can therefore be seen from FIG. 8 that the precise location of the processing of outputs from any of the primary sensors 98 (and/or secondary sensors 104) can be varied. It is, however, desirable in some embodiments, as noted previously, to position the sensor suite boards 56 close to their associated primary sensor 98 in order to more accurately detect the impact of various parameters on the associated primary sensor 98.

Propulsion system 58 of FIG. 8 includes a host subsystem 132. Host subsystem 132, in some embodiments, includes the primary controller 94a, force sensors 98a, and propulsion motor(s) 96 of propulsion system 58 of FIG. 6. In such embodiments, host subsystem 132 and sensor suite board 56g together act in any of the same manners previously described above with respect to propulsion system 58 of FIG. 6. However, in alternative embodiments, host subsystem 132 may omit primary controller 94a and instead utilize the secondary controller of sensor suite board 56g for controlling propulsion motor(s) 96. FIG. 8 therefore illustrates that it is not necessary to include a primary controller 94 for each system. Instead, a system such as propulsion system 58 can utilize the secondary controller (108) and/or main controller 100 to perform the primary function associated with a particular system.

Although secondary sensors 104 have been primarily described herein for use with the primary sensors 98 of three specific systems (propulsion system 58, scale/exit detection system 76, and deck articulation system 78), it will be understood by those skilled in the art that one or more of the sensor suite boards 56 described herein may be used with a variety of other types of primary sensors 98 and/or with a variety of other types of systems. The following chart identifies a number of additional examples of the types of primary sensors 98 with which one or more of the sensor suite boards 56 disclosed herein may be used in order to enhance the function of the primary sensors and/or for other purposes. This chart identifies several different parameters that may be detected by the primary sensor(s) 98, as well as a corresponding patent and/or patent application that provides further details regarding how the primary sensor is constructed, operates, and/or is integrated into a patient support apparatus. Each of these patents and patent applications is incorporated herein by reference in their entirety, and it will be understood by those skilled in the art that sensor suite boards 56 of the type disclosed herein may be added to any of the patient support apparatuses disclosed in these references in order to enhance the function of the primary sensors and patient support apparatuses disclosed therein.

| Parameters Detected by Primary Sensor(s) | Patent/App. | Filing Date | Title |
|---|---|---|---|
| Patient's heart rate, breathing rate, and other vital signs | 7,699,784 | Jul. 5, 2007 | System for Detecting and Monitoring Vital Signs |
| Patient sleep quantity, quality, and other | 9,320,444 | Mar. 14, 2014 | Patient Support Apparatus with |

| Parameters Detected by Primary Sensor(s) | Patent/App. | Filing Date | Title |
|---|---|---|---|
| sleep parameters | | | Patient Information Sensors |
| Patient interface pressures, vital signs, | 61/449,182 | Mar. 4, 2011 | Sensing System for Patient Supports |
| Patient movement | 14/692,871 | Apr. 22, 2015 | Person Support Apparatus with Position Monitoring |
| Patient and object weights, movement, and position | 14/873,734 | Oct. 2, 2015 | Person Support Apparatus with Motion Monitoring |
| A patient's activity, time out of bed, number of steps, and other activity data | 14/928,513 | Oct. 30, 2015 | Person Support Apparatus with Patient Mobility Monitoring |
| Patient turns, bed sore assessment scores, eating and sleeping, exit detection system status, etc. | 14/578,630 | Dec. 22, 2014 | Video Monitoring System |
| Patient vital signs, position, movement | 15/346,779 | Nov. 9, 2016 | Person Support Apparatus with Acceleration Detection |
| Patient mobility score and/or assessments | 15/809,351 | Nov. 10, 2017 | Patient Support Apparatuses with Mobility Assessment |
| Cleanliness and/or usability status of a patient support apparatus | 15/709,586 | Sep. 20, 2017 | Systems and Methods for Determining the Usability of Person Support Apparatuses |

It will also be understood that the use of the term "transceiver" herein is intended to cover not only devices that include a transmitter and receiver contained within a single unit, but also devices having a transmitter separate from a receiver, and/or any other devices that are capable of both transmitting and receiving signals or messages.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
a frame;
a support surface adapted to a support a patient thereon;
a primary sensor adapted to output measurements of a force exerted on a component of the patient support apparatus, wherein the primary sensor is a load cell configured to output the force measurements with an acceptable accuracy level over a range of force values applied to the primary sensor;
a primary controller adapted to receive the force measurements from the primary sensor;
a suite of secondary sensors adapted to measure a plurality of secondary parameters capable of affecting the force measurements made by the primary sensor, the suite of secondary sensors excluding any load cells; and
a secondary controller adapted to process outputs from the suite of secondary sensors to detect if the force exerted on the component of the patient support apparatus is outside of the range of force values.

2. The patient support apparatus of claim 1 wherein the secondary controller is further adapted to send a notification to the primary controller if the secondary controller detects that the force exerted on the component of the patient support apparatus is outside of the range of force values.

3. The patient support apparatus of claim 1 wherein the suite of secondary sensors includes at least two of the following: a humidity sensor, a pressure sensor, a gyroscope, a magnetometer, an accelerometer, a speed sensor, a temperature sensor, or an angle sensor.

4. The patient support apparatus of claim 1 wherein the primary sensor is adapted to detect a weight of a patient supported on the support surface and the suite of secondary sensors includes an accelerometer adapted to detect acceleration of the load cell.

5. The patient support apparatus of claim 1 wherein the primary controller and the suite of secondary sensors are mounted to a common circuit board.

6. The patient support apparatus of claim 1 further comprising:
a second primary sensor adapted to measure a second primary parameter related to a second component of the patient support apparatus; and
a second suite of secondary sensors adapted to measure a second plurality of secondary parameters, the second plurality of secondary parameters being the same as the plurality of secondary parameters.

7. A patient support apparatus comprising:
a frame;
a support surface adapted to a support a patient thereon;
a scale system including a plurality of load cells adapted to detect a weight of a patient supported on the support surface, wherein a first one of the load cells is adapted to output a first signal indicative of a first force applied to the first load cell in a vertical direction when a first force sensing direction of the first load cell is aligned with the vertical direction, and a second one of the load cells is adapted to output a second signal indicative of a second force applied to the second load cell in the vertical direction when a second force sensing direction of the second load cell is aligned with the vertical direction;
a first sensor adapted to measure a first angle indicative of a first misalignment of the first force sensing direction with the vertical direction;

a second sensor adapted to measure a second angle indicative of a second misalignment of the second force sensing direction with the vertical direction; and a controller adapted to use the first and second angles to correct any errors introduced into the first and second signals from the first and second misalignments.

8. The patient support apparatus of claim 7 wherein the first sensor is coupled to a first circuit board positioned adjacent the first load cell, and the second sensor is coupled to a second circuit board positioned adjacent the second load cell.

9. The patient support apparatus of claim 7 further comprising:

a first sensor suite associated with the first load cell, the first sensor suite adapted to measure a plurality of non-weight parameters of the first load cell; and a second sensor suite associated with the second load cell, the second sensor suite adapted to also measure the plurality of non-weight parameters of the second load cell;

wherein the plurality of non-weight parameters includes at least one of the following: humidity, air pressure, angular acceleration, linear acceleration, speed, temperature, geomagnetic orientation, position, or an angle.

10. The patient support apparatus of claim 9 wherein the first sensor suite is mounted to a first circuit board and the second sensor suite is mounted to a second circuit board, the first sensor suite being positioned adjacent to the first load cell and the second circuit board being positioned adjacent to the second load cell.

11. The patient support apparatus of claim 9 wherein the first load cell is coupled to a first beam and the first sensor suite includes a first and a second accelerometer adapted to detect bending of the first beam, and the second load cell is coupled to a second beam and the second sensor suite includes a third and a fourth accelerometer adapted to detect bending of the second beam.

12. A patient support apparatus comprising:

a frame;

a support surface adapted to a support a patient thereon;

a first primary sensor adapted to measure a first primary parameter related to a first component of the patient support apparatus;

a first suite of secondary sensors adapted to measure a first plurality of characteristics of the first primary sensor, each of the first plurality of characteristics being different from the first primary parameter, wherein the first suite of secondary sensors is mounted to a first circuit board positioned adjacent the first primary sensor;

a primary controller adapted to use the first primary parameter to control the patient support apparatus; and a secondary controller adapted to process outputs from the first suite of secondary sensors to detect if an error exists in a measurement of the first primary parameter.

13. The patient support apparatus of claim 12 wherein the first plurality of characteristics of the first primary sensor include at least two of the following: an angle of the first primary sensor, a pressure experienced by the first primary sensor, an acceleration of the first primary sensor, a speed of the first primary sensor, a temperature of the first primary sensor, an ambient humidity of the first primary sensor, a geographical orientation of the first primary sensor, or a change in orientation of the first primary sensor.

14. The patient support apparatus of claim 12 further comprising:

a second primary sensor adapted to measure a second primary parameter related to a second component of the patient support apparatus;

a second suite of secondary sensors adapted to measure a second plurality of characteristics of the second primary sensor, each of the second plurality of characteristics being different from the second primary parameter; and wherein each of the second suite of secondary sensors is mounted to a second circuit board positioned adjacent the second primary sensor, and the secondary controller is further adapted to process outputs from the second suite of secondary sensors to detect if an error exists in a measurement of the first primary parameter.

15. The patient support apparatus of claim 14 wherein the secondary controller is coupled directly to the first and second suites of secondary sensors such that outputs from the secondary sensors of both the first and second suites of secondary sensors are routed to the secondary controller without relying on the primary controller.

16. The patient support apparatus of claim 14 further comprising:

a wheel;

a motor adapted to drive the wheel; and wherein the first primary sensor is a force sensor adapted to detect a user-applied force and the primary controller is adapted to control the motor based on outputs from the force sensor.

17. The patient support apparatus of claim 16 wherein the second primary sensor is a force sensor adapted to detect a weight of a patient supported on the support surface.

* * * * *